United States Patent
Yun et al.

(10) Patent No.: US 9,775,689 B2
(45) Date of Patent: Oct. 3, 2017

(54) ADJUSTABLE DENTAL IMPLANT

(71) Applicant: GEO-PROTECTOR TECH. CO., LTD., Kaohsiung (TW)

(72) Inventors: Ping Yun, Kaohsiung (TW); Tobey Tsai, Kaohsiung (TW); Benson Yun, Kaohsiung (TW); Thomas Lee, Kaohsiung (TW)

(73) Assignee: GEO-PROTECTOR TECH. CO., LTD., Kaohsiung (TW)

( * ) Notice: Subject to any disclaimer, the term of this patent is extended or adjusted under 35 U.S.C. 154(b) by 0 days.

(21) Appl. No.: 15/079,457

(22) Filed: Mar. 24, 2016

(65) Prior Publication Data
US 2017/0049538 A1 Feb. 23, 2017

(30) Foreign Application Priority Data
Aug. 17, 2015 (TW) .............................. 104126760 A

(51) Int. Cl.
*A61C 8/00* (2006.01)
(52) U.S. Cl.
CPC .......... *A61C 8/0031* (2013.01); *A61C 8/0009* (2013.01); *A61C 8/0022* (2013.01); *A61C 8/0092* (2013.01)
(58) Field of Classification Search
CPC ... A61C 8/0031; A61C 8/0009; A61C 8/0022; A61C 8/0092
See application file for complete search history.

(56) References Cited

U.S. PATENT DOCUMENTS

| | | | |
|---|---|---|---|
| 8,540,513 B1* | 9/2013 | Aldoukhi | A61C 8/0018 433/172 |
| 2006/0084033 A1* | 4/2006 | Gittleman | A61C 8/0001 433/173 |
| 2011/0195379 A1* | 8/2011 | Allaire | A61C 8/0048 433/174 |
| 2011/0287386 A1* | 11/2011 | Better | A61C 8/0018 433/174 |
| 2012/0045736 A1* | 2/2012 | Shimko | A61C 8/0006 433/173 |
| 2012/0202173 A1* | 8/2012 | Seo | A61O 5/70 433/220 |
| 2014/0248583 A1* | 9/2014 | Rostami | A61C 8/0012 433/173 |

* cited by examiner

*Primary Examiner* — Nicholas Lucchesi
(74) *Attorney, Agent, or Firm* — Rabin & Berdo, P.C.

(57) ABSTRACT

An adjustable dental implant comprises an implant body, a connecting structure, and two wings. The implant body comprises a fixture and an abutment. The fixture comprises a top, a bottom, a peripheral surface connected between the top and the bottom, and a joining portion formed on the peripheral surface. The abutment is set on the top of the fixture. The connecting structure is set between the fixture and the abutment. The wings are pivotally connected with two opposite sides of the connecting structure. Or, one of the wings is pivotally connected with the connecting structure, and the other wing is fixed with the connecting structure. The wing or the wings may be adjusted to fit the surface of the cortical bone. Dental posts are allowed to penetrate the alveolar bone entirely to secure the fixture.

17 Claims, 15 Drawing Sheets

ADJUSTABLE DENTAL IMPLANT

BACKGROUND

1. Technical Field

The present invention relates to an adjustable dental implant for implantation in the alveolar bone and allowing a dental crown to be mounted thereon.

2. Description of the Prior Art(s)

Osseointegration dominates the bonding strength between the alveolar bone and a dental implant, whether a one-piece dental implant or a two-piece dental implant. Take the two-piece dental implant for instance. The dental implant comprises a fixture and an abutment. The fixture is screwed with the alveolar bone. The bottom of the abutment is screwed with the top of the fixture. The top of the abutment extends beyond the gum flap that covers the alveolar bone, so as to mount a dental crown.

As the dental implant is integrated with the alveolar bone only by the fixture in a dental implantation surgery, the quality and quantity of the alveolar bone has a great influence on the success and safety of the dental implantation surgery. Clinically, an alveolar bone at least 10 millimeters in height and at least 5 millimeters in width leads to a successful and safe dental implantation surgery. However, the tooth is extracted or exfoliates before the dental implantation surgery. The alveolar bone atrophies or loses, or the sinus lifts after the tooth extraction and the tooth exfoliation, such that the quality and quantity of the alveolar bone declines, introducing the following issues:

First, the dental implant is likely to damage the tissues near the alveolar bone, resulting in the failure of the dental implantation surgery.

Second, the dental implant cannot be firmly integrated with the alveolar bone and the osseointegration is not ideal. The dental implant and the alveolar bone are loosened after a period of applying the occlusal force on the dental crown, causing the falling of the dental implant and the dental crown and the failure of the dental implantation.

In order to avoid the issues mentioned above, the inventors of the present invention provided a dental implant comprising a fixture, an abutment set at the top of the fixture, and a connecting structure set between the fixture and the abutment. The connecting structure comprises two opposite wings. Each of the wings is at a predetermined angle toward the fixture. The fixture is implanted in the alveolar bone for osseointegration. The top of the abutment extends beyond the gum flap for mounting a dental crown thereon. The wings cover the surface of the cortical bone of the alveolar bone and are fixed with the cortical bone by dental posts.

Clinically, the dental implant provided by the inventors of the present invention has been proved to be capable of avoiding the issues mentioned above, convenient, cost-effective, and safe for implantation. Especially, at the positions where the alveolar bone is poor in quality and insufficient in quantity such as the positions with thin sinus, the one-piece or two-piece dental implant cannot be implemented.

Nevertheless, the degree of alveolar bone atrophy differs case by case. The wings arranged at the predetermined angles toward the fixture are not applicable to all cases. Further, for orientation of abutment for required occlusion, the predetermined angles of the wings may not entirely fit with the surface of the cortical bone and thus the dental posts are not allowed to penetrate the alveolar bone entirely. As such, dental posts are incapable of providing sufficient strength to securely fasten the fixture at a proper position in the process of osseointegration.

To overcome the shortcomings, an adjustable dental implant to mitigate or obviate the aforementioned problems is provided.

SUMMARY

An objective of the present invention is to provide an adjustable dental implant to overcome the technical limitation in fixing the fixture at a proper position in the process of osseointegration.

In accordance with one of the embodiments, the adjustable dental implant comprises an implant body, a connecting structure, and two wings. The implant body comprises a fixture and an abutment. The fixture comprises a top, a bottom, a peripheral surface connected between the top and the bottom, and a joining portion formed on the peripheral surface. The abutment is set on the top of the fixture. The connecting structure is set between the fixture and the abutment. The wings are connected with two opposite sides of the connecting structure. Each of the wings has at least one through hole. One of the wings is pivotally connected with the connecting structure.

In accordance with one of the embodiments, another wing is pivotally connected with the connecting structure.

In accordance with one of the embodiments, another wing is fixed with the connecting structure.

The fixture is implanted in the alveolar bone. The joining portion is connected with the alveolar bone for osseointegration. The wings are fixed with the cortical bone by dental posts to fix the fixture at the initial stage of the osseointegration. For severe alveolar ridge atrophy, the bone graft (the autogenic bone graft or the bone substitute) fills the space between the cortical bone of the alveolar bone and the wings participate in the osseointegration to secure the adjustable dental implant in the alveolar bone. The wings act as a fence to confine the bone graft for avoiding loosening and displacement of the bone graft. As such, the width and the height of the alveolar ridge may be reconstructed. Besides, depending on degree of the atrophy of the alveolar bone, the adjustable dental implant may be directly applied to bone graft surgery or sinus lift surgery during implantation.

Further, the wing or the wings pivotally connected with the connecting structure may be adjusted according to the morphology of alveolar bone and fit with the surface of the cortical bone. Dental posts are allowed to penetrate the alveolar bone entirely, so as to securely fix the fixture. Accordingly, the adjustable dental implants contribute to rapid reconstruction of the elders' occlusion.

After the fixture of the adjustable dental implant, which comprises one wing pivotally connected with one side of the connecting structure and another wing fixed with the opposite side of the connecting structure, is disposed in the bone hole, the wing fixed with the connecting structure is fixed with one side of the alveolar bone first; then the wing pivotally connected with the connecting structure is laminated on and fixed with another side of the alveolar bone. Accordingly, the adjustable dental implant is instantly and stably fixed at the initial stage of the implantation, simplifying operation of the implantation.

In accordance with one of the embodiments, the joining portion of the fixture is a screw thread. When the surgical site of the alveolar bone has a lamina dura with a critical safe thickness, which is from 6 mm to 8 mm, the fixture is fastened with the alveolar bone at the surgical site. The wings are laminated on the alveolar bone, and then fixed with the alveolar bone by dental posts. The joining portion may provide stable and sufficient strength, allowing the adjustable dental implant to osseointegrate with the alveolar bone smoothly and have enough bearing force at the initial stage of the osseointegration. The patient's needs on beauty and occlusion are both met.

When the alveolar bone adjacent to the maxillary sinus is thin, a dental implant has a great chance to stray into the maxillary sinus, thereby causing severe sequela and medical disputes, and jeopardizing the mutual trust between the dentist and patient. In view of this, in accordance with some of the embodiments, the connecting structure is detachably mounted on the implant body. The wings are laminated on the alveolar bone and fixed with the alveolar bone by dental posts first. And then the fixture of the implant body is implanted in the surgical site of the alveolar bone under the guiding of the connecting structure, thereby protecting and preventing the adjustable dental implant from straying into the maxillary sinus.

Other objectives, advantages, and novel features of the embodiments of the present invention will become more apparent from the following detailed description when taken in conjunction with the accompanying drawings.

DETAILED DESCRIPTION

Figure 7:
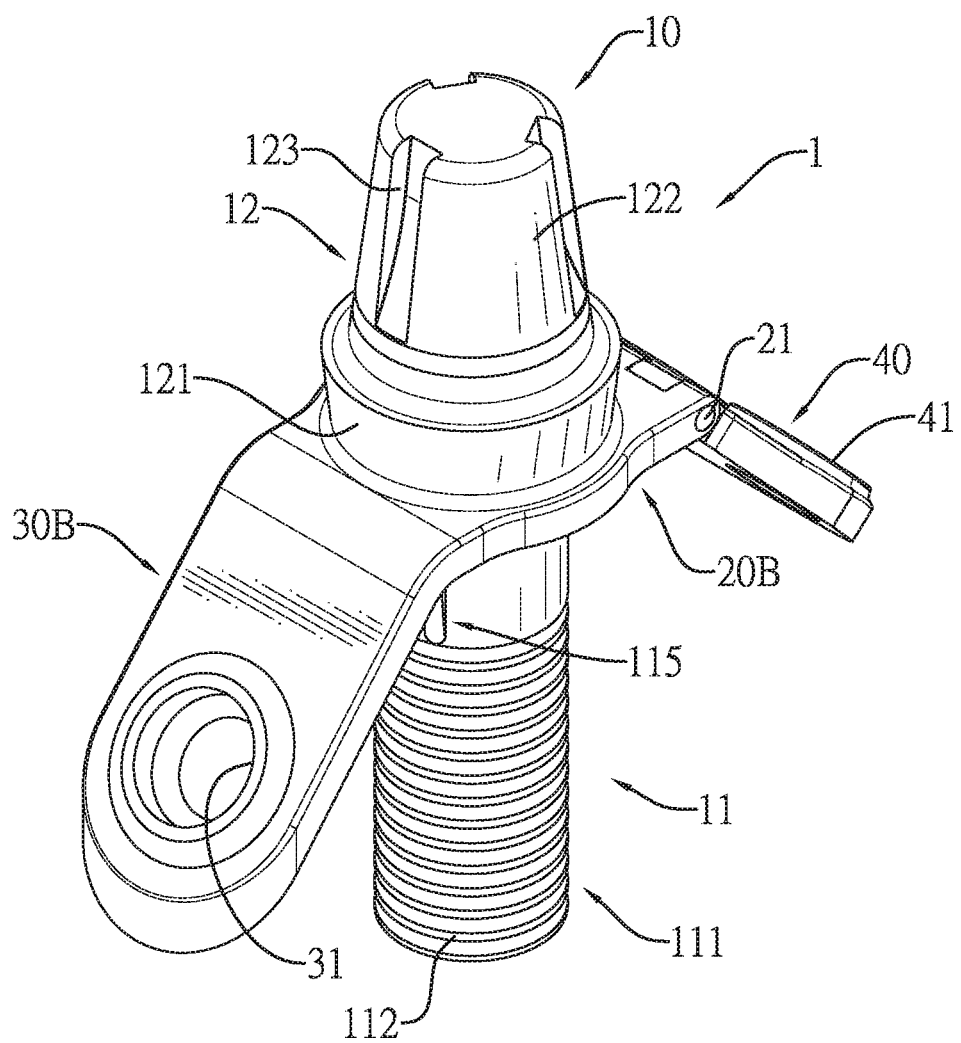
FIG. 7 is a perspective view of a third embodiment of an adjustable dental implant in accordance with the present invention.

Several embodiments, the first to fifth embodiments, of the adjustable dental implant of the present invention are respectively demonstrated in FIGS. 1, 4, 7, 9, and 11. In each of the embodiments, the adjustable dental implant comprises an implant body 10, a connecting structure 20A, 20B, 20C, 20D, and two wings 30A, 30B, 40. The two wings are a first wing 30A (as shown in FIGS. 1, 4, 9, and 11), 30B (as shown in FIG. 7) and a second wing 40.

With reference to FIGS. 1, 4, 7, 9, and 11, the implant body 10 comprises a fixture 11 and an abutment 12. The fixture 11 may be implanted in the alveolar bone for osseointegration. The length of the fixture 11 can be modified depending on needs. The fixture 11 comprises a top, a bottom, and a peripheral surface connected between the top and the bottom. The abutment 12 is formed on the top of the fixture 11 for allowing a dental crown mounted thereon.

With reference to FIGS. 1, 4, 7, 9, and 11, the fixture 11 comprises a joining portion 111 formed on the lower section of the peripheral surface. The joining portion 111 is uneven with protrusive and recessed parts. As embodiments demonstrated in FIGS. 1 and 7, the joining portion 111 is consisted of multiple circular recesses 112 arranged longitudinally at spaced intervals on the peripheral surface. As embodiments demonstrated in FIGS. 4, 5, 9, 11, and 12, the joining portion 111 is formed with a screw thread 113 around the peripheral surface of the joining portion 111, and a longitudinal notch 110 is formed on the lower section of the peripheral surface and extends toward the bottom of the fixture 11. A blade 114 is connected between the longitudinal notch 110 and the screw thread 113. In an embodiment, the joining portion may be formed on the peripheral surface entirely.

Figure 1:
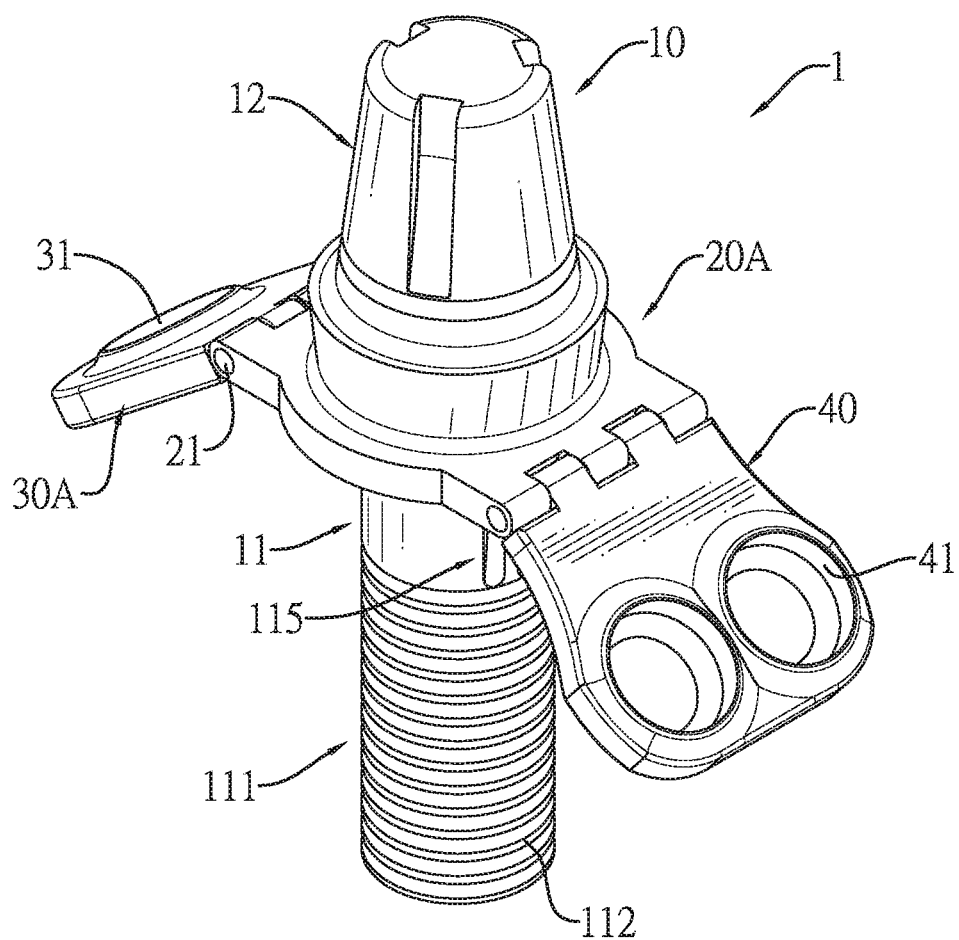
FIG. 1 is a perspective view of a first embodiment of an adjustable dental implant in accordance with the present invention.
Figure 3:
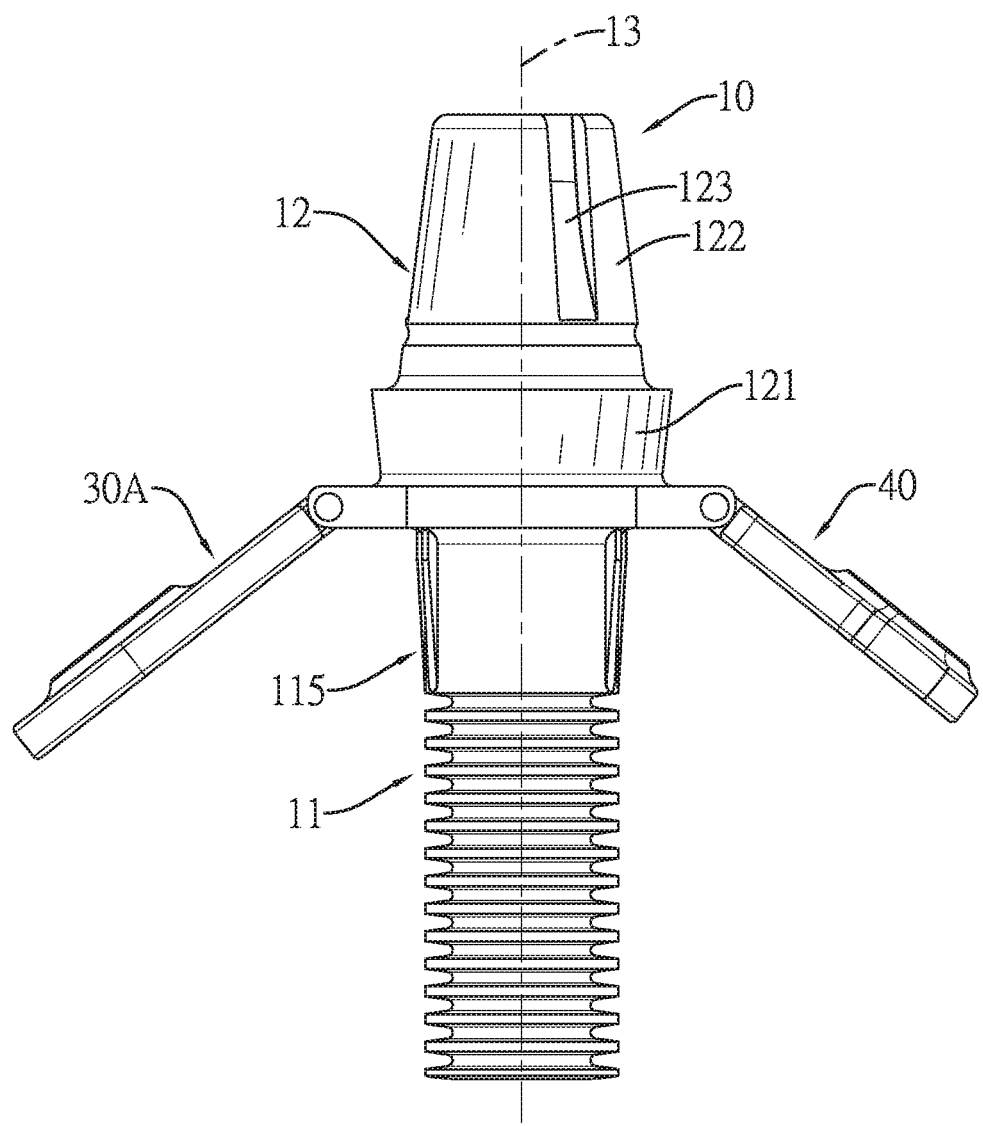
FIG. 3 is a lateral view of the first embodiment of the adjustable dental implant in FIG. 1.
Figure 4:
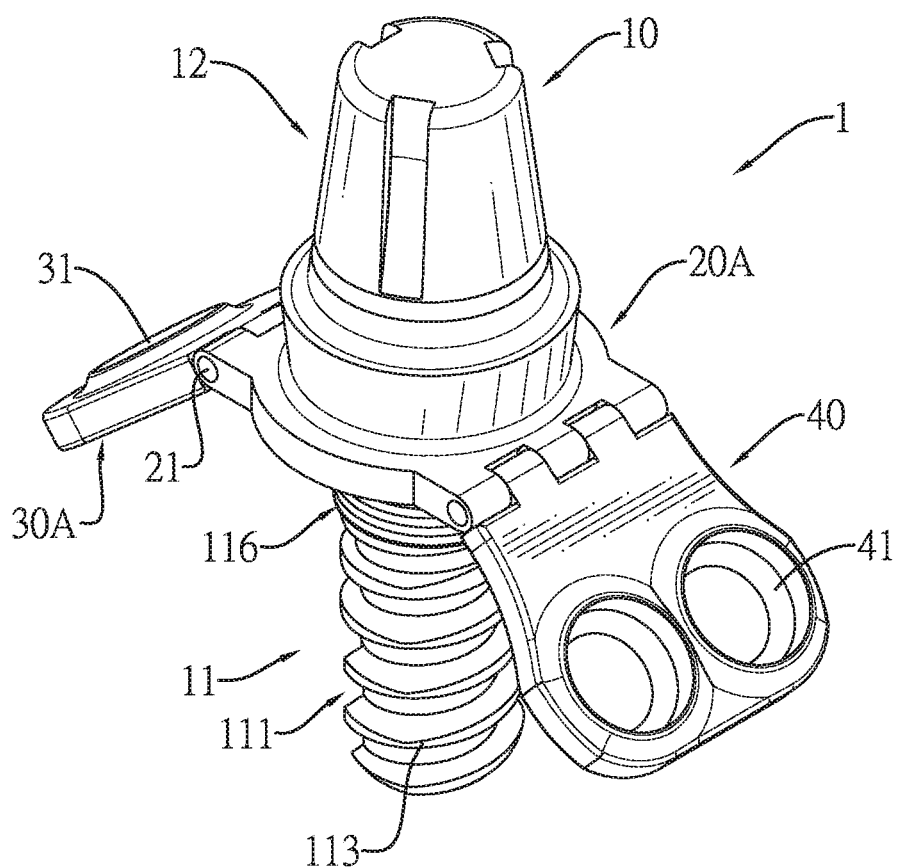
FIG. 4 is a perspective view of a second embodiment of an adjustable dental implant in accordance with the present invention.
Figure 8:
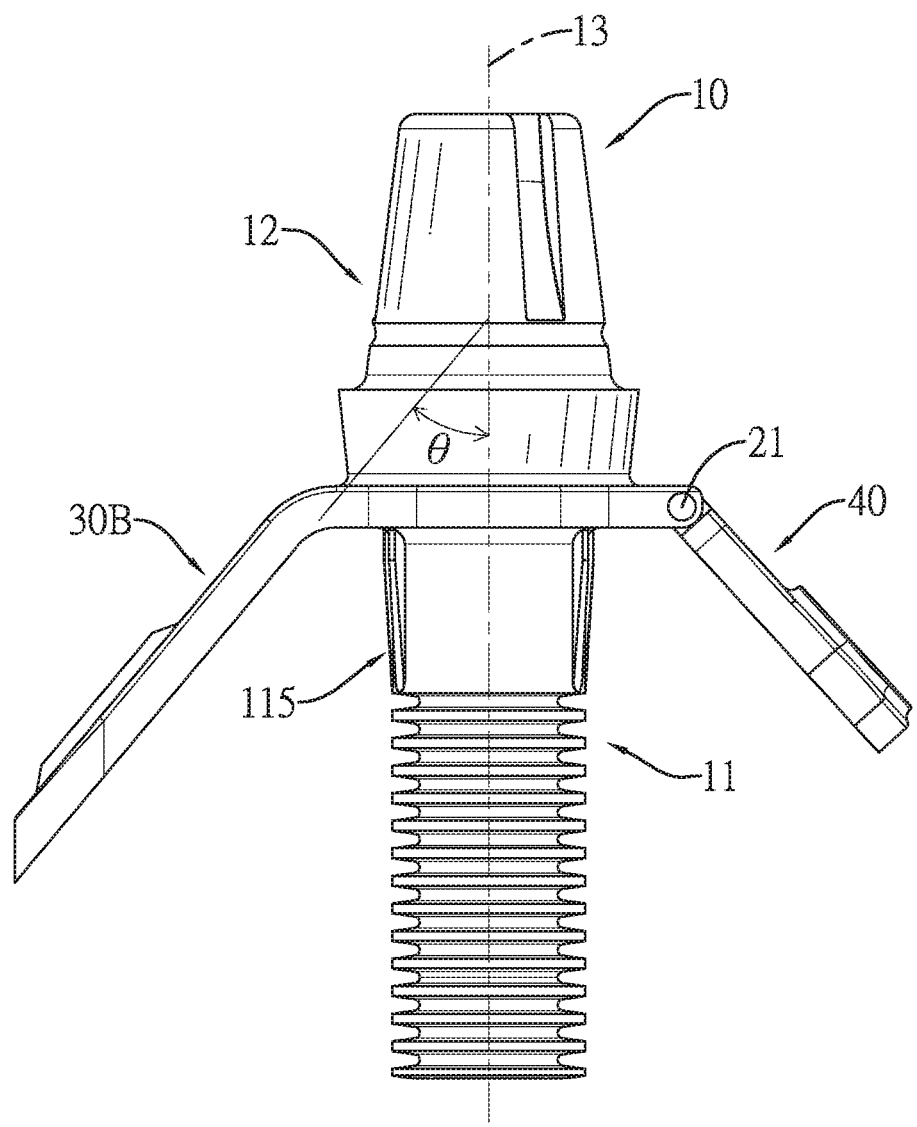
FIG. 8 is a lateral view of the third embodiment of the adjustable dental implant in FIG. 7.
Figure 9:
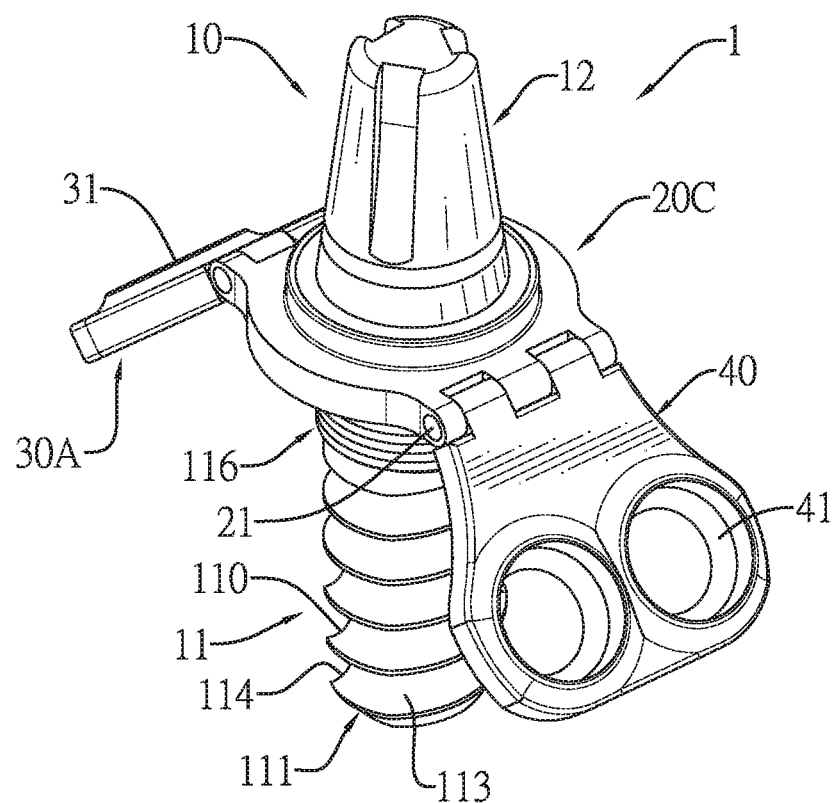
FIG. 9 is a perspective view of a fourth embodiment of an adjustable dental implant in accordance with the present invention.
Figure 10:
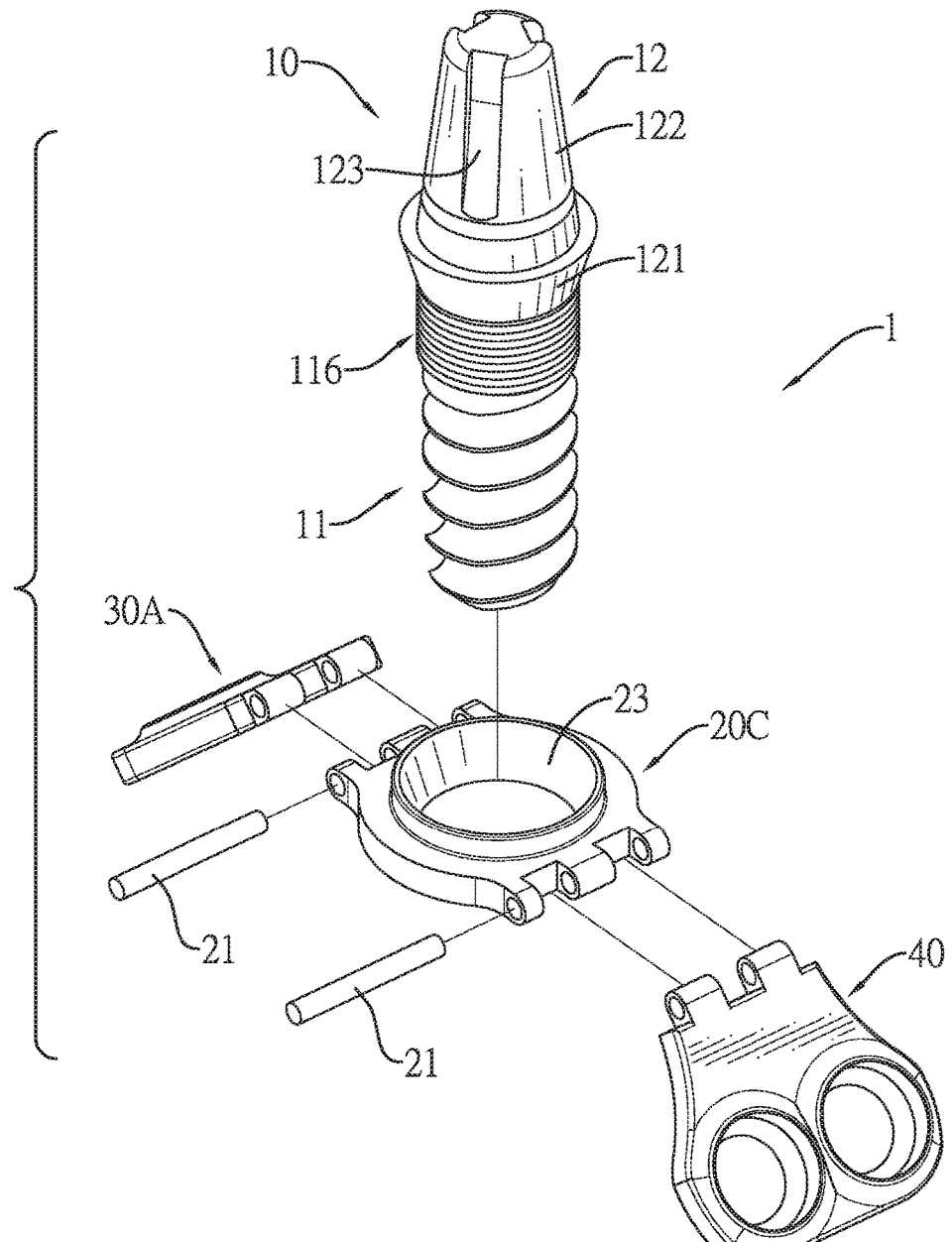
FIG. 10 is an exploded perspective view of the fourth embodiment of the adjustable dental implant in FIG. 9.
Figure 11:
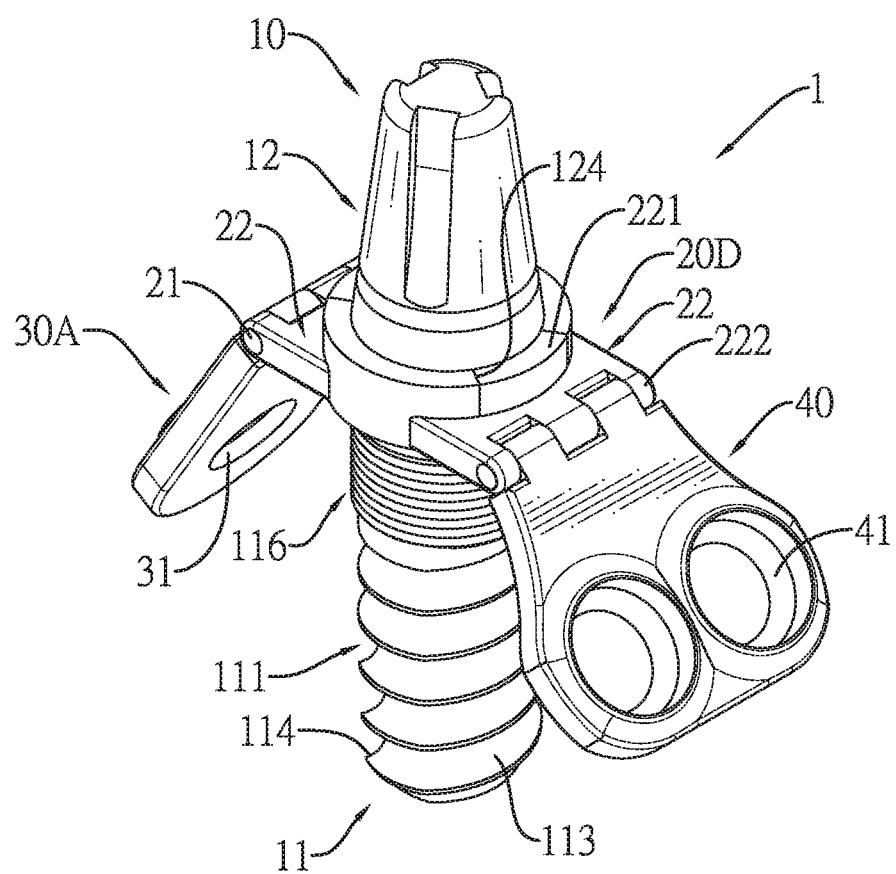
FIG. 11 is a perspective view of a fifth embodiment of an adjustable dental implant in accordance with the present invention.

The fixture 11 comprises a combination portion 115 (as shown in FIGS. 1 and 7), 116 (as shown in FIGS. 4, 9, and 11) formed on the upper section of the peripheral surface and located at the upper side of the joining portion 111. As demonstrated in FIGS. 2, 3, 7, and 8, the combination portion 115 is consisted of multiple elongated protrusions parallel to the center axis 13 of the implant body 10. The elongated protrusions are arranged equiangularly on the peripheral surface, or each two of the elongated protrusions are arranged on the peripheral surface along the radial direction of the fixture 11. In an embodiment, each of the elongated protrusions has a width progressively increasing downwardly; that is, the elongated protrusions are tapered. As demonstrated in FIGS. 5, 6, 10, and 12, the combination portion 116 is consisted of multiple annular protrusions or multiple spiral protrusions surrounding the peripheral surface.

With reference to FIGS. 2, 3, 5, 7, 10, and 12, the abutment 12 comprises a base 121, an abutment post 122, and multiple mounting recesses 123. The base 121 comprises a lower end connected with the top of the fixture 11, an upper end opposite the lower end, and a side surface connected between the lower end and the upper end. The abutment post 122 is formed on the upper end of the base 121. The abutment post 122 is tapered and has a diameter progressively increasing downwardly. Each of the mounting recesses 123 is formed transversely in and extends longitudinally along the abutment post 122. Each of the mounting recesses 123 is inclined downwardly and outwardly. In some embodiments, the mounting recesses 123 are arranged equiangularly on the abutment post 122.

Figure 2:
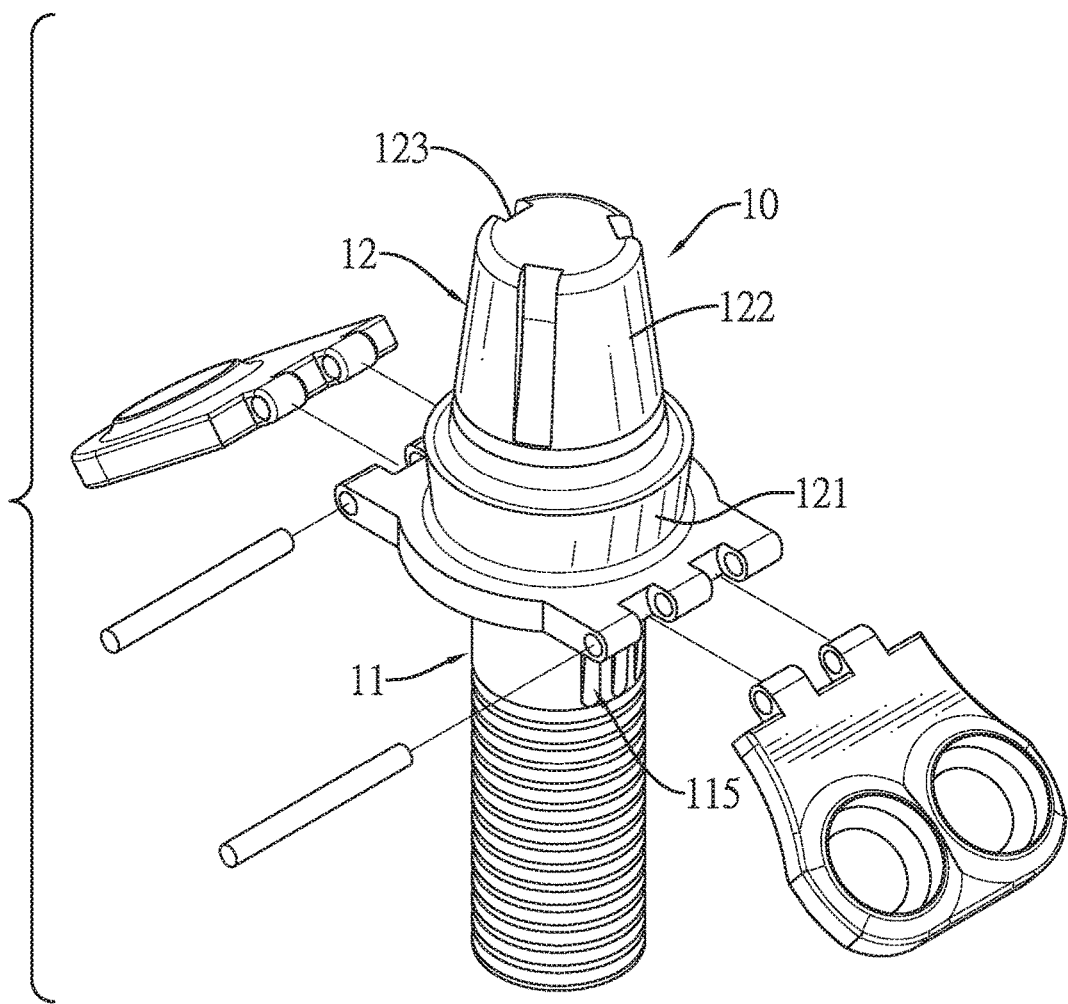
FIG. 2 is an exploded perspective view of the first embodiment of the adjustable dental implant in FIG. 1.
Figure 5:
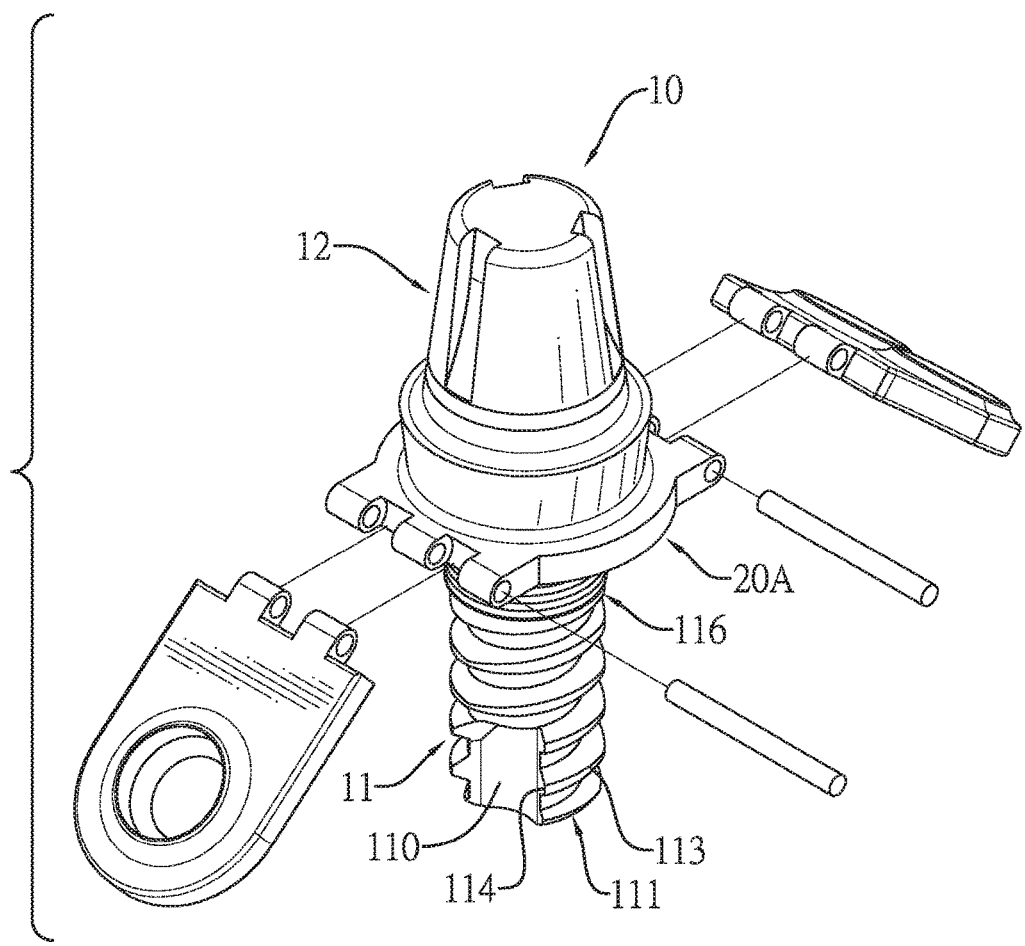
FIG. 5 is an exploded perspective view of the second embodiment of the adjustable dental implant in FIG. 4.

The connecting structure 20A (as shown in FIGS. 1 and 4), 20B (as shown in FIG. 7), 20C (as shown in FIG. 9), 20D (as shown in FIG. 11) is set between the fixture 11 and the abutment 12. As demonstrated in FIGS. 2, 5, and 7, the connecting structure 20A (as shown in FIGS. 2 and 5), 20B (as shown in FIG. 7), and the implant body 10 are integrated as one single part. As demonstrated in FIG. 10, the connecting structure 20C is composed of one element, and is detachably mounted between the fixture 11 and the abutment 12. As demonstrated in FIG. 12, the connecting structure 20D is composed of multiple elements, and is detachably mounted between the fixture 11 and the abutment 12. In an embodiment, the connecting structure is composed of one element or multiple elements, and is fixed between the fixture and the abutment.

The first wing 30A (as shown in FIGS. 1, 4, 9, and 11), 30B (as shown in FIG. 7) and the second wing 40 are disposed at two opposite sides of the connecting structure 20A (as shown in FIGS. 1 and 4), 20B (as shown in FIG. 7), 20C (as shown in FIG. 9), 20D (as shown in FIG. 11). Each of the first wing 30A, 30B and the second wing 40 has at least one through hole 31, 41. As demonstrated in FIGS. 7 and 8, one of the first wing 30B and the second wing 40 is pivotally connected with the connecting structure 20B via a pivot 21, while the other wing is fixed with the connecting structure 20B. As demonstrated in FIGS. 1, 4, 9 and 11, each of the first wing 30A and the second wing 40 is pivotally connected with the connecting structure 20A (as shown in FIGS. 1 and 4), 20B (as shown in FIG. 7), 20C (as shown in FIG. 9), 20D (as shown in FIG. 11) via a pivot 21.

Figure 6:
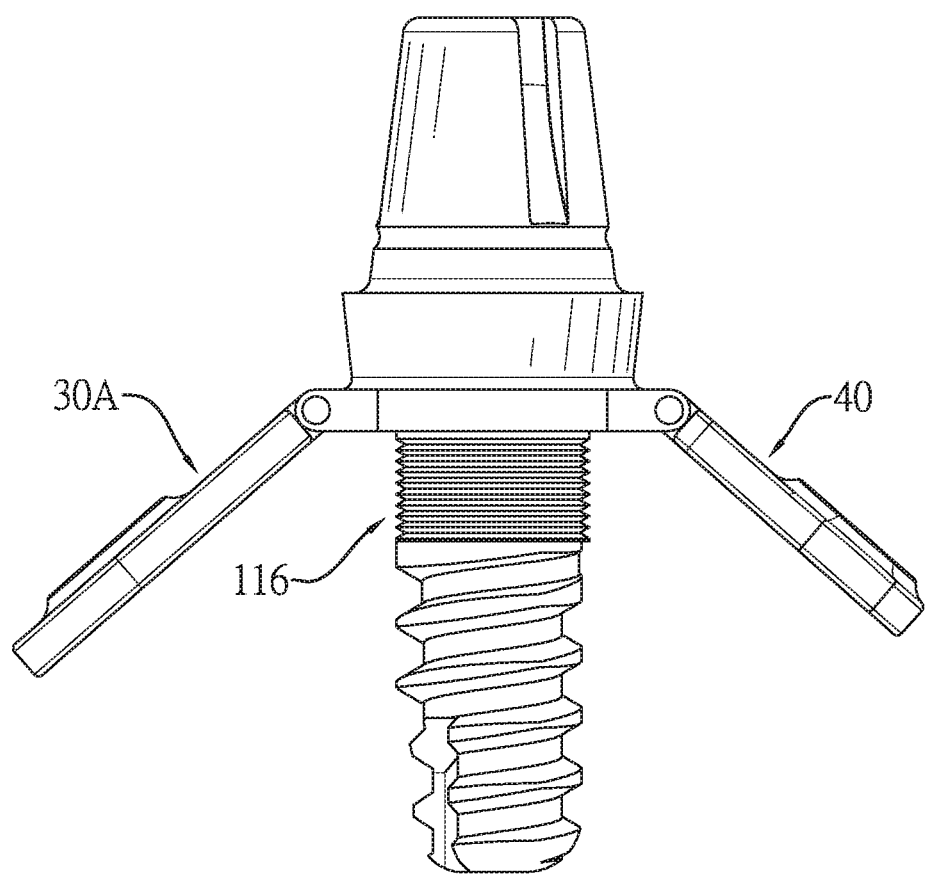
FIG. 6 is a lateral view of the second embodiment of the adjustable dental implant in FIG. 5.

The length of the first wing may be different from or equal to the length of the second wing. As demonstrated in FIGS. 3, 6, and 8, the length of the first wing 30A (as shown in FIGS. 3 and 6), 30B (as shown in FIG. 8) is different from the length of the second wing 40.

The width of the first wing may be different from or equal to the width of the second wing 40. For example, as demonstrated in FIG. 1, when the first wing 30A has a larger width than the second wing 40, the first wing 30A has one through hole 31 and the second wing 40 has two through holes 41.

In an embodiment demonstrated in FIGS. 7 and 8, the connecting structure 20B, the fixture 11, and the abutment 12 are integrated as one single part. Or the connecting structure 20B is made of one element and is fixed between the fixture 11 and the abutment 12. The first wing 30B and the connecting structure 20B are integrated as one single part. The first wing 30B is inclined downwardly, and an acute angle θ is formed between the first wing 30B and the center axis 13 of the implant body 10. The degree of the acute angle θ depends on needs. In the present embodiment, preferably, the acute angle θ is, but not limited to, from 10° to 45°. For instance, the acute angle θ may be 10°, 20°, 25°, 30°, 35°, 40°, and 45°. The second wing 40 is pivotally connected with the connecting structure 20B via the pivot 21.

In an embodiment demonstrated in FIGS. 9 and 10, the connecting structure 20C is an annular element. The connecting structure 20C is fitted around the implant body 10 and between the fixture 11 and the abutment 12. Further, the base 121 is taper-shaped and has a diameter progressively decreasing from the upper end to the lower end. The connecting structure 20C has a tapered hole 23 corresponding in shape to the side surface of the base. The connecting structure 20C is fitted around the base 121 of the implant body 10. Each of the first wing 30A and the second wing 40 is pivotally connected with the connecting structure 20C via the pivot 21.

Figure 12:
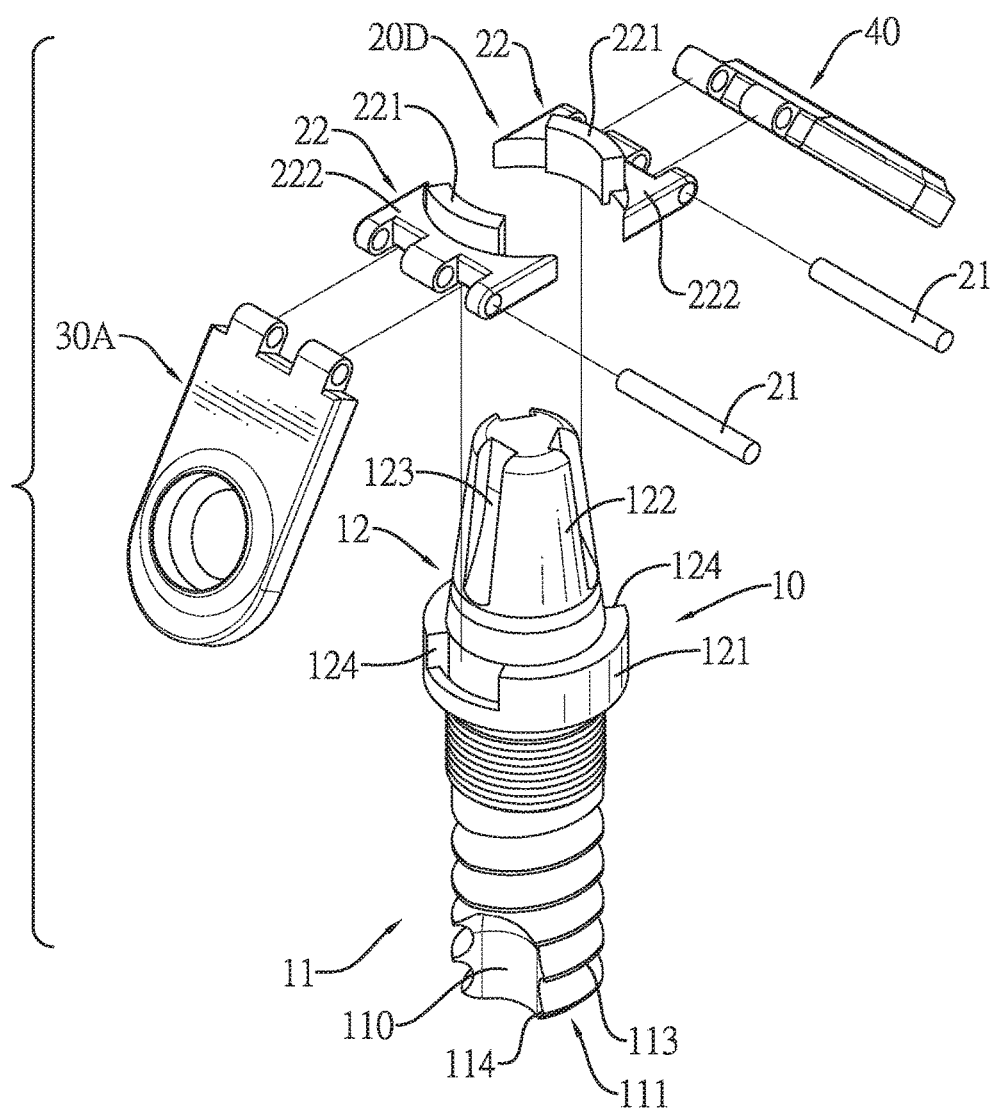
FIG. 12 is an exploded perspective view of the fifth embodiment of the adjustable dental implant in FIG. 11.

In an embodiment demonstrated in FIGS. 11 and 12, the abutment 12 comprises two mortises 124 formed on two opposite sides of the base 121. The connecting structure 20D comprises two connecting blocks 22. Each of the connecting blocks 22 comprises a tenon 221 and a connecting portion 222 opposite the tenon 221. The tenons 221 of the connecting blocks 22 are embedded in the mortises 124 respectively. The connecting portion 222 of the connecting blocks 22 are pivotally connected with the first wing 30A and the second wing 40 respectively via the pivot 21.

Figure 13:
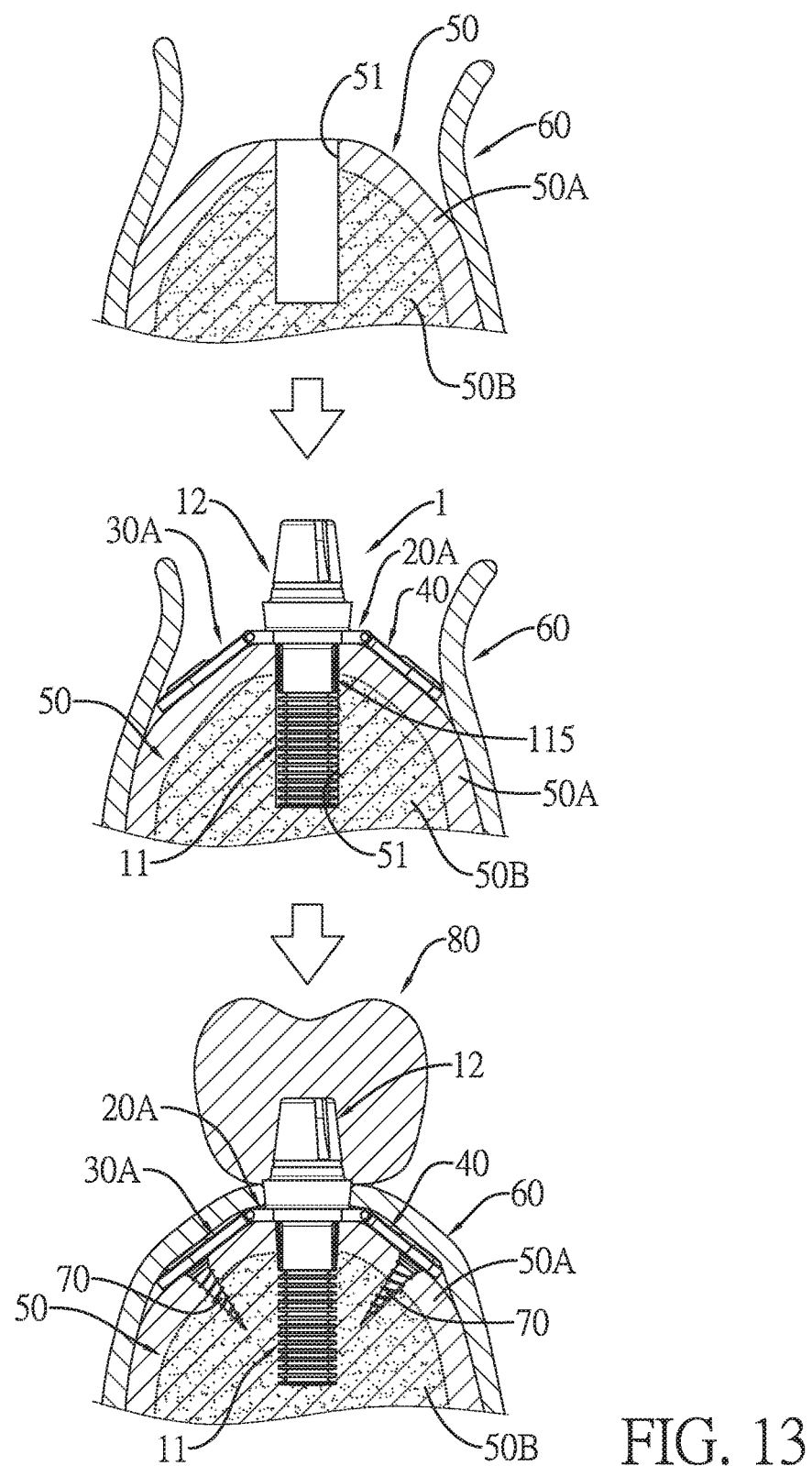
FIG. 13 is a schematic view of implanting the adjustable dental implant of FIG. 1 into the alveolar bone and mounting a dental crown.

With reference to FIG. 13, the adjustable dental implant 1 is applied to the dental implantation surgery. After the patient's gum is anesthetized locally by the dentist, the gum flap 60 where a tooth has exfoliated is cut and lifted with a scalpel to expose the alveolar bone 50 covered by the gum flap 60. A surgical site of the alveolar bone 50 selected by dental radiography or three-dimensional optical coherence tomography is drilled to form a bone hole 51. The fixture 11 is implanted in the bone hole 51. Further, the alveolar bone 50 comprises an outer layer called cortical bone 50A and an inner layer called cancellous bone 50B. The bone hole 51 is formed through the cortical bone 50A and into the cancellous bone 50B. Moreover, the combination portion 115 may be embedded in the bone hole 51 and abut the alveolar bone 50 to strengthen the connection between the fixture 11 and the alveolar bone 50, thereby enhancing the osseointegration of the fixture 11 and the alveolar bone 50.

Afterwards, the first wing 30A and the second wing 40 are laminated on two sides of the surface of the cortical bone 50A. Dental posts 70 are mounted through the first wing 30A and the second wing 40 and locked with the alveolar bone 50. Since the first wing 30A and the second wing 40 are pivotally connected with the connecting structure 20A, the first wing 30A and the second wing 40 may be fittingly adjusted to laminate on the alveolar bone 50. The dental posts 70 may provide desired locking effect between the adjustable dental implant 1 and the alveolar bone 50.

After covering the alveolar bone 50, the first wing 30A, and the second wing 40, the gum flap 60 is stitched. The top of the abutment 12 extends beyond the gum flap 60 for mounting a dental crown 80 thereon.

Generally, the alveolar bone at least 10 millimeters in height and at least 5 millimeters in width leads to safe dental implantation surgery with a success rate of 95% to 98%. However, the atrophy or the loss of the alveolar bone after the tooth extraction and exfoliation varies case by case, so the quality and quantity of the alveolar bone varies case by case also. Therefore, the means to implant the adjustable dental implant 1 varies case by case. When the surgical site of the alveolar bone has a lamina dura with a critical safe thickness (from 6 mm to 8 mm), for example, the adjustable dental implant 1 demonstrated in FIG. 4 or 9 may be applied. The bone hole is drilled to have an aperture smaller than the diameter of the fixture 11. The fixture 11 is fixed with the alveolar bone by the screw thread 113 to strengthen the connection between the fixture 11 and the alveolar bone.

Under the circumstance that the quality and quantity of the alveolar bone is inferior, the dental implantation surgery using the adjustable dental implant may be adjoined with bone grafting to have the fixture of the adjustable dental implant sunk into the alveolar bone. Further, when the thickness of the alveolar bone is thin, sinus lifting and bone grafting may be adjoined with the dental implantation surgery to provide an ideal osseointegration area between the adjustable dental implant and the alveolar bone.

Figure 14:
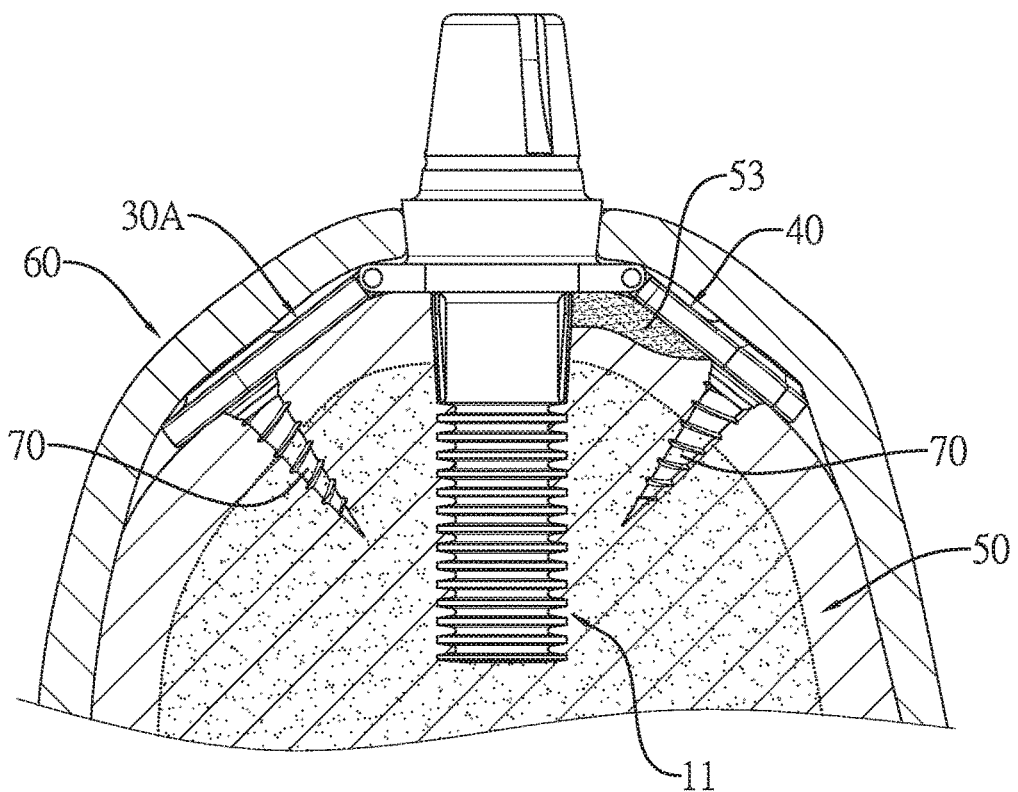
FIG. 14 is a schematic view of filling a bone graft and implanting the adjustable dental implant of FIG. 1 into the alveolar bone.

When the dental implantation surgery is operated with the alveolar bone having bad quality or/and insufficient quantity, the autogenic bone graft produced with the drilling to form the bone hole shall be preserved. With reference to FIG. 14, after the dental posts 70 are mounted through the first wing 30A and the second wing 40 and locked with the alveolar bone 50, the space between the fixture 11, the second wing 40, and the alveolar bone 50 is filled with a bone graft 53 to reconstruct the alveolar ridge. The bone graft 53 may be the said autogenic bone graft produced during drilling of the bone hole. Besides, when the autogenic graft produced with the drilling of the bone hole is insufficient to fill up the space, the space may be further filled with autogenic bone graft or bone piece obtained from other sites of the alveolar bone 50 or the bone substitute to reconstruct the alveolar ridge and avoid loss and displacement of the autogenic bone graft produced with the drilling of the bone hole, thereby enhancing the osseointegration between the fixture 11 and the alveolar bone 50. Afterwards, the gum flap 60 covers the alveolar bone 50, the first wing 30A, and the second wing 40, and then is stitched.

Figure 15:
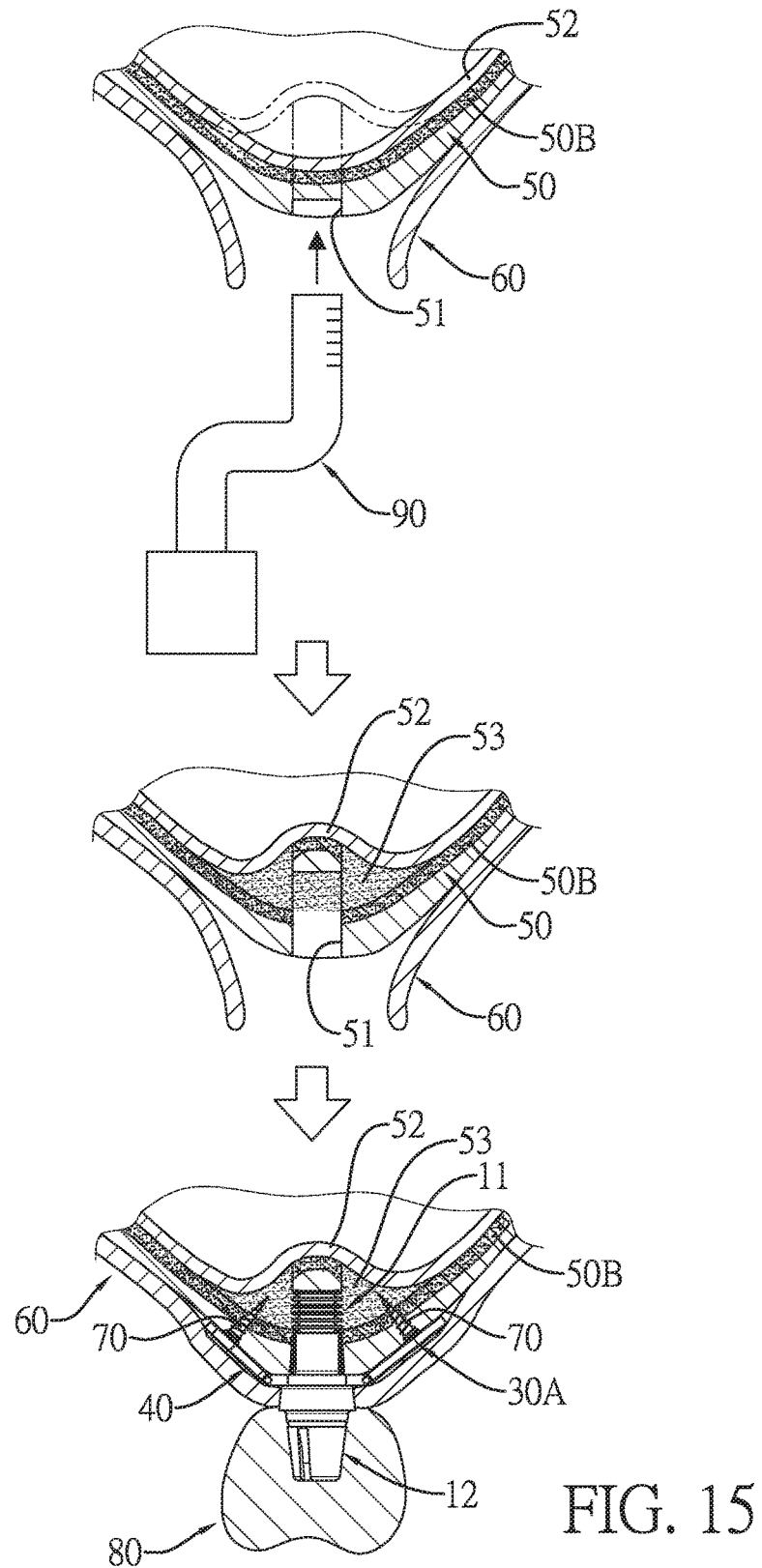
FIG. 15 is a schematic view of implanting the adjustable dental implant of FIG. 1 into the alveolar bone adjacent to a maxillary sinus and mounting a dental crown.

With reference to FIG. 15, when the thickness of the alveolar bone 50 is thin, the sinus lifting may be adjoined with the dental implantation surgery to provide an ideal osseointegration area between the adjustable dental implant and the alveolar bone 50. The drilling to form the bone hole 51 is ceased while accessing the sinus membrane 52. An osteotome 90 is inserted into the bone hole 51 and compresses the sinus membrane 52. Once the sinus membrane 52 is loosened, the compression by the osteotome 90 is ceased. A room is formed between the sinus membrane 52 and the cancellous bone 50B of the alveolar bone 50. The bone graft 53 is filled into the room. The bone graft 53 may be the said autogenic bone graft produced with the drilling of the bone hole 51. The fixture 11 of the adjustable dental implant is implanted in the bone hole 51. The first wing 30A and the second wing 40 are laminated on two sides of the surface of the cortical bone 50A. Dental posts 70 are mounted through the first wing 30A and the second wing 40 and locked with the alveolar bone 50. Afterwards, the gum flap 60 covers the alveolar bone 50, the first wing 30A, and the second wing 40, and then is stitched. The top of the abutment 12 extends beyond the gum flap 60 for mounting a dental crown 80 thereon.

When the alveolar bone adjacent to the maxillary sinus is thin, a dental implant has a great chance to stray into the maxillary sinus. With reference to FIGS. 9 to 12, the connecting structure 20C, 20D is detachably mounted on the implant body 10. After the surgical site of the alveolar bone is selected, the first wing 30A and the second wing 40 are fixed with the cortical bone of the alveolar bone by dental posts first. And then the fixture 11 of the implant body 10 is implanted in the bone hole at the surgical site with the guiding of the connecting structure 20C, 20D, thereby protecting and preventing the adjustable dental implant 1 straying into the maxillary sinus.

In a dental implantation surgery, the adjustable dental implant in accordance with the embodiments is implanted into the alveolar bone by the fixture. The joining portion of the fixture is osseointegrated with the alveolar bone. The combination portion of the fixture may be embedded in and abuts the alveolar bone. The first wing and the second wing are laminated on the cortical bone and fixed by dental posts. Accordingly, the adjustable dental implant is securely fixed with the alveolar bone, and the abutment extends beyond the gum flap for mounting a dental crown thereon.

In addition, the wing or the wings pivotally connected with the connecting structure may be adjusted according to the morphology of alveolar bone and fit with the surface of the cortical bone. Dental posts are allowed to penetrate the alveolar bone entirely to firmly fix the fixture. Accordingly, the adjustable dental implants contribute to rapid reconstruction of the elders' occlusion.

Based on the above, the adjustable dental implant in accordance with the embodiments may be implanted with convenient operation, so the surgical time is shortened and the infection rate is lowered. In addition, the fixture of the adjustable dental implant is securely fixed with the alveolar bone after the osseointegration, thereby supporting the abutment firmly and increasing the bite force. Therefore, the adjustable dental implants contribute to rapid reconstruction of elders' occlusion.

What is claimed is:

1. An adjustable dental implant comprising:
   an implant body comprising:
      a fixture comprising:
         a top;
         a bottom opposite the top;
         a peripheral surface connected between the top and the bottom;
         a combination portion formed on an upper section of the peripheral surface; and
         a joining portion formed on the peripheral surface; and
      an abutment on the top of the fixture, the abutment comprising:
         a base comprising:
            a lower end connected with the top of the fixture; and
            an upper end opposite the lower end;
         an abutment post formed on the upper end of the base, having a tapered shape, and having a diameter progressively increasing downwardly; and
         multiple mounting recesses formed transversely in and extending longitudinally along the abutment post, and each of the mounting recesses inclined downwardly and outwardly;
   a connecting structure set between the fixture and the abutment; and
   a first wing and a second wing respectively connected with two opposite sides of the connecting structure, each of the first wing and the second wing having at least one through hole, and the first wing pivotally connected with the connecting structure.

2. The adjustable dental implant as claimed in claim 1, wherein the second wing is pivotally connected with the connecting structure.

3. The adjustable dental implant as claimed in claim 2, wherein the connecting structure and the implant body are integrated as one single part.

4. The adjustable dental implant as claimed in claim 2, wherein the connecting structure is composed of one element and is assembled between the fixture and the abutment.

5. The adjustable dental implant as claimed in claim 4, wherein:
   the base comprises a side surface connected between the lower end of the base and the upper end of the base;
   the upper end of the base has a diameter larger than a diameter of the lower end of the base; and
   the connecting structure is fitted around the base, and is an annular element having a tapered hole, and the tapered hole corresponds in shape to the side surface.

6. The adjustable dental implant as claimed in claim 2, wherein the abutment comprises two mortises opposite each other, and the connecting structure comprises two connecting blocks, each of the connecting blocks is connected between one of the mortises and one of the wings, and each of the connecting blocks comprises:
   a tenon embedded in the mortise; and a connecting portion being opposite the tenon and pivotally connected with the wing.

7. The adjustable dental implant as claimed in claim 1, wherein the second wing is fixed with the connecting structure.

8. The adjustable dental implant as claimed in claim 7, wherein the connecting structure and the implant body are integrated as one single part.

9. The adjustable dental implant as claimed in claim 7, wherein the connecting structure is composed of one element and is assembled between the fixture and the abutment.

10. The adjustable dental implant as claimed in claim 9, wherein:
   the base comprises a side surface connected between the lower end of the base and the upper end of the base;
   the upper end of the base has a diameter larger than a diameter of the lower end of the base; and
   the connecting structure is fitted around the base, and is an annular element having a tapered hole, and the tapered hole corresponds in shape to the side surface.

11. The adjustable dental implant as claimed in claim 1, wherein the connecting structure and the implant body are integrated as one single part.

12. The adjustable dental implant as claimed in claim 1, wherein the connecting structure is composed of one element and is assembled between the fixture and the abutment.

13. The adjustable dental implant as claimed in claim 12, wherein:
   the base comprises a side surface connected between the lower end of the base and the upper end of the base;
   the upper end of the base has a diameter larger than a diameter of the lower end of the base; and
   the connecting structure is fitted around the base, and is an annular element having a tapered hole, and the tapered hole corresponds in shape to the side surface.

14. The adjustable dental implant as claimed in claim 1, wherein the joining portion is consisted of multiple circular recesses spaced from each other and arranged longitudinally at spaced intervals on the peripheral surface.

15. The adjustable dental implant as claimed in claim 1, wherein the joining portion is a screw thread, and the fixture comprises:
   a longitudinal notch formed on a lower section of the peripheral surface and extending toward the bottom of the fixture; and
   a blade connected between the longitudinal notch and the joining portion.

16. The adjustable dental implant as claimed in claim 1, wherein the joining portion is consisted of multiple circular recesses spaced from each other and arranged from the upper section of the peripheral surface to the lower section of the peripheral surface, the combination portion is consisted of multiple elongated protrusions parallel to a center axis of the implant body, and each of the elongated protrusions has a width progressively increasing downwardly.

17. The adjustable dental implant as claimed in claim 1, wherein the joining portion is formed with a screw thread, the combination portion is consisted of multiple annular protrusions or multiple spiral protrusions surrounding the peripheral surface, and the fixture comprises:
   a longitudinal notch formed on the lower section of the peripheral surface and extending toward the bottom of the fixture; and
   a blade connected between the longitudinal notch and the joining portion.

\* \* \* \* \*